United States Patent [19]

Lützen

[11] Patent Number: 5,470,566
[45] Date of Patent: Nov. 28, 1995

[54] SOLID ORAL ANTICARIOGENIC COMPOSITION

[75] Inventor: Claude E. Lützen, Vejle, Denmark

[73] Assignee: Fertin Laboratories A/S (Dansk Tyggegummi Fabrik A/S), Dandyvej

[21] Appl. No.: 402,774

[22] Filed: Mar. 9, 1995

Related U.S. Application Data

[63] Continuation of Ser. No. 27,936, Mar. 8, 1993, abandoned, which is a continuation of Ser. No. 799,869, Nov. 27, 1991, abandoned, which is a continuation of Ser. No. 445,903, Dec. 4, 1989, abandoned, which is a continuation of Ser. No. 396, filed as PCT/DK86/00050, May 7, 1986, abandoned.

[30] Foreign Application Priority Data

May 10, 1985 [DK] Denmark ................... 2092/85

[51] Int. Cl.$^6$ .............. A61K 7/16; A61K 7/22
[52] U.S. Cl. ................. 424/54; 424/49
[58] Field of Search ............... 424/54, 49

[56] References Cited

U.S. PATENT DOCUMENTS

| | | | |
|---|---|---|---|
| 168,857 | 7/1960 | King | 424/54 |
| 3,060,098 | 10/1962 | Gershon | 424/57 |
| 3,957,967 | 5/1976 | L'Orange | 424/54 |
| 4,302,441 | 11/1981 | Mühlemann | 424/48 |
| 4,627,977 | 12/1986 | Gaffar | 424/48 |

FOREIGN PATENT DOCUMENTS

| | | |
|---|---|---|
| 0124804 | 10/1944 | Australia . |
| 3011182 | 10/1980 | Germany . |
| 0673670 | 5/1949 | United Kingdom . |

OTHER PUBLICATIONS

Gershon et al in Cosmetics: Science and Technology, Second Edition, edited by Balsam et al, Wiley–Interscience, a division of John Wiley & Sons, Inc., N.Y. 1972, pp. 449–451.

*Primary Examiner*—Howard E. Schain
*Attorney, Agent, or Firm*—Donald S. Dowden

[57] ABSTRACT

A solid, oral, anticariogenic composition in the form of a chewing gum or a lozenge and beyond the conventional chewing gum or lozenge ingredients containing as dental plaque acid-neutralizing ingredient urea in an amount from 0.5% by weight to 80% by weight, based on the total weight of the composition, an optional coating not being taken into account.

The composition is used for reducing the risks of dental caries subsequently to eating and drinking as it causes a neutralization of the plaque acids.

2 Claims, No Drawings

SOLID ORAL ANTICARIOGENIC COMPOSITION

This is a continuation of application Ser. No. 08/027,936, filed Mar. 8, 1993, not abandoned, which was a continuation of application Ser. No. 07/799,869, filed Nov. 27, 1991, now abandoned, which was a continuation of application Ser. No. 07/445,903, filed Dec. 4, 1989, now abandoned, which was a continuation of application Ser. No. 07/000,396, filed as PCT/DK86/00050, May 7, 1986, now abandoned.

FIELD OF THE INVENTION

The invention relates to a solid oral anticariogenic composition in the form of chewing gums or lozenges. More particularly, the present invention relates to an anticariogenic product to be used for neutralizing the acid produced in dental plaque subsequent to eating or drinking.

DESCRIPTION OF THE PRIOR ART

The prior art has long sought a means to control the cariogenic effect of comestibles and sweetened beverages and the like.

Several ways exist of protecting the teeth against bacterial attacks. In order to explain the latter please find below a short description of the caries theory accepted today.

The mouth is a biological environment usually being well-balanced. When the food has entered the mouth it isdivided into fine particles by the teeth at the same time as it is softened by the saliva. The biological environment includes furthermore the microflora existing in the mouth.

The above microflora includes bacteria, especially a certain group of bacteria, viz. the facultative anaerobes, capable of decomposing carbohydrates in the absence of oxygen into organic acids, especially lactic acid. The acid attacks the dental enamel and the underlying dentine which causes a demineralisation. A reaction implies that a thin layer of the enamel is dissolved. Repeated reactions may cause caries or a "hole in the tooth". The critical pH-value of demineralisation is 5.5. Below this value the enamel and the underlying dentine are dissolved. Above a pH of 5.5 the enamel and the dentine are remineralised.

The remineralisation comprises a regeneration of dentine and enamel by components from the saliva. The demineralisation must not, however, be too advanced if a successful remineralisation is to be obtained.

A demineralisation of the teeth requires the presence in the mouth of facultative anaerobic bacteria, carbohydrate, water, anaerobic conditions, as well as the correct temperature. If these conditions do not exist the process does not take place.

Thus different ways of preventing formation of caries exist.

It is possible to avoid anaerobic conditions by removing plaque (tooth-cleaning for instance by means of a tooth brush, dental floss, toothpicks or by polishing). The resistance of the enamel to acid attacks can be increased for instance by a fluorine treatment (brushing the teeth by means of a fluorine-containing toothpaste, rinsing or swabbing with a fluorine-containing agent). The facultative anaerobic bacteria can be inactivated for instance by intervening in the glycolysis.

It is possible to ensure that the acid produced is neutralized as quickly as possible. Finally the production of saliva can be stimulated in order to improve the cleaning of the teeth, "the defence mechanism of nature itself". During the latest decades much has been done for teaching the population dental care, especially eating less sweets and brushing teeth by means of fluorine-containing toothpaste at least twice a day. Furthermore fluorine has in certain areas been added to the drinking water. In spite of these measures caries still arises. The fluorine toothpaste reduces the caries frequency by 30%–40% provided the teeth are carefully brushed twice a day.

The largest caries risk group is children with newly erupted permanent teeth. Especially many children do not brush their teeth as regularly as they ought to. West German investigations have shown that for instance in 1970/ 1971 1% of the children never brushed their teeth, and 10% of the children brushed their teeth irregularly. Among 2/3 of the teeth-brushing children each brushing took less than 1 minute. Furthermore many children often eat sugar-sweetened products, which happens frequently between the regular meals and under circumstances making it difficult to brush the teeth afterwards.

Under particular circumstances where an actual brushing of the teeth is difficult or impossible, such as after lunch, after snacks, and in connection with long meetings and when travelling, adults can also have a need for an easy possibility of cleaning their teeth.

Thus an essential need exists for a means applicable in an easy and practical manner as a suitable supplement to the daily tooth-brushing. Attempts at fulfilling the above need are already known.

As a result sugar-free chewing gum exists which has been sweetened especially by sorbitol as the sorbitol is not decomposed into organic acids under normal conditions and thus does not cause a risk of formation of caries but in the usual way increases the secretion of saliva. The advantage of such a product is that it is harmless to the teeth, but the chewing of sugar-free chewing gum of this type does not involve an active caries prophylaxis.

Beyond being an ingredient in toothpaste the fluorine has also been used in mouthwash, lozenges, and chewing gums.

Especially the chewing gum is suitable for being brought along in the pocket or the-bag. However, as previously mentioned the fluorine can only increase the resistance of the enamel against acid attacks to a certain degree. Furthermore the toxicological aspects in connection with intake of fluorine must be considered.

Attempts have also been made of using various alkaline substances for the neutralization of acid, cf. e.g. Norwegian Patent No. 46,152 from 1929 concerning a chewing gum composition containing magnesia oxide, but due to the taste the products containing such substances were never a success.

JADA 96:651–655, 1978 describes a triennial clinical study of chewing gum containing trimethaphosphate. The results were not satisfactory.

C. T. Grove and C. J. Grove 1934: "The biological aspect of dental caries". Dent. Cosmos 76: 1029 and C. J. Grove and C. T. Grove 1935: "Chemical study of human saliva indicating that ammonia is an immunizing factor in dental caries." *J. Amer. dent. Ass.* 22: 247 believed that ammonia —which they assumed derived from the urea of the saliva —was responsible for the caries immunity of human beings. They imagined that ammonia acted by reducing the formation of plaque. Various other scientists were, however, incapable of proving this relationship between a tendency to form caries and the concentration of ammonia in the saliva (J. White and R. W. Bunting, 1935: "An investigation into the possible relationship of ammonia in the saliva to dental caries."

J. Amer. dent. Ass. 22: 468, G. E. Youngburg, 1935–36: "Salivary ammonia and its relation to dental caries." J. dent. Res. 15: 247. M. Karshan, 1936: "Factors in human saliva correlated with the presence and activity of dental caries." J. dent. Res. 15: 383–293).

I. Kleinberg and G. N. Jenskins 1964: "The pH of dental plaques in different areas of the mouth before and after meals and their relationship to the pH and rate of flow of resting saliva." In Archs. oral Biol. 9: 493–516, it was shown that in vivo plaque pHs are above the saliva pH and the hypothesis was set forth that the above is due to the fact that plaque bacterial ureases convert saliva urea into ammonia. This theory was supported by T. M. Hassel 1972: "The effect of acetohydroxamic acid on interdental pH assessed with radio telemetry." Helv. odont. Acta 16: 27–31, where a pH drop in mouthwater and interdental plaque upon use of urease inhibitor were shown by in vivo studies.

R. M. Stephan 1940: "Two factors of possible importance in relation to the etiology and treatment of dental caries and other dental diseases." Science 92: 578–579, was of the opinion that ammonia from urea in the saliva would cause a neutralization of part of the plaque acids produced after intake of carbohydrate-containing food. Furthermore he described that the pH in plaque on tooth surfaces and in cavities rose to 8.5 upon rinsing with a concentrated carbamide solution (synthetic urea).

Clinical tests with dentifrices containing urea and ammonium salts gave contradictory results and interest waned rapidly (for a review see B. Regolati 1971: "Ammonia and urea in oral pathophysiology—a literature review" Helv. odont. Acta 15: suppl. 7, pp 139–146).

In a reprint of Sveriges Tandläkarförbunds Tidning No. 8, 1963, G. Frostell and I. Erickson have described the addition of urea to carbohydrate-containing food such as sweets, chocolates, marmelades, confectioneries as a possible means for controlling caries. They concluded that an elimination or reduction, if any, of the caries-producing effect of carbohydrate-containing food could possibly be obtained if the articles of food contain urea. Later tests carried out by some of the most recognized scientists within the anticariogenic field gave, however, the conclusion that urea is inactive as far as a reduction of plaque and caries is concerned, cf. A. R. Firestone et al., Caries Res. 16: 112–117, 1982. While urea is stated to be inactive, urea hydrogen peroxide and hydrogen peroxide are on the contrary stated to be very effective for reducing plaque accumulation and the frequency of caries. U.S. Pat. No. 4,302,441, Hans R. Mühlemann et al., states that solid oral glycerol-free preparations containing active urea hydrogen peroxide are effective for counteracting acids formed by fermentable carbohydrates in dental plaque. Both above publications are about 20 years later than the previously mentioned reprint and both reveal a direct prejudice against urea per se being applicable for preparing an efficient anticariogenic composition. Unlike the flatter, urea hydrogen peroxide is considered applicable for formulating efficient, stable oral preparations as the above late tests all ascribe the anticariogenic effect to the hydrogen peroxide part.

At present two dentifrice chewing gum products containing solid urea hydrogen peroxide are on the market in Denmark, viz. V6⁺® produced by Fertin Laboratories A/S and Caroxin® produced by Ferrosan, the latter product having been on the market since 1927, and it appears from the Danish catalogue of medicines that $H_2O_2$ is considered being the active ingredient in both said products. Tests have proved that these products are active by intake after intermediary meals since at quickly chewing they cause an increase of the plaque pH to a level above the previously mentioned critical pH of 5.5 for the demineralisation. In a Directive 76/768 concerning cosmetics the EEC commission has, however, prohibited the addition of hydrogen peroxide to compositions for internal use.

GB Patent No. 673,670 discloses dentrifices for neutralizing the acid in dental plaque including chewing gums containing urea and urease. Such chewing gums containing urease must be prepared and stored under strictly moisture-free conditions and the processing temperature must be kept below 50°60° C. to avoid denaturation leading to inactivation of the urease.

Water must be present by the conventional process for the preparation of chewing gum and during the mixing process the temperature rises to 60° C. and locally to 80°, and the chewing gum proposed in GB Patent No. 673,670 can consequently not be prepared by the conventional process without decomposition of the urea and urease.

The preparation of said proposed urease-containing chewing gum product in moisture-free form and using a mixing temperature below 50° C. would be difficult and the resulting product would certainly have unsatisfactory organoleptic properties. During the entire preparation the product must be surrounded by a dry atmosphere corresponding to the necessary conditions for preparing effervescent tablets. It is very expensive to establish such conditions and the rooms having the necessary low humidity are unpleasant for the production staff.

Furthermore, it is necessary to provide for cooling during the mixing and extrusion process to ensure that the temperature does not exceed 50° C. in order to avoid denaturation and decomposition of the urease. Such cold mixing temperatures make it very difficult and expensive to obtain a homogeneous product.

Finally, a product containing both urea and urease will require a special moisture-proof package, which should probably also contain a desiccant, e.g. in the form of a tablet.

OBJECTS AND SUMMARY OF THE INVENTION

It has now turned out surprisingly that unlike the other bases present in the saliva, urea can be used as the only active ingredient of a solid oral anticariogenic composition in the form of chewing gums or lozenges. Such a composition solves the above problems described concerning an easy access to a supplementary dental care without risks for the health and without the bad taste arising when using other bases.

Furthermore the composition fulfils the demand given by the Directire 76/768 concerning cosmetics of the EEC commission for a product replacing the previous hydrogen peroxide-containing products.

Finally, the products according to the invention may be produced without special measures under conventional conditions by means of conventional equipment for producing chewing and lozenges, respectively. This makes the production more inexpensive and less complicated than the production of e.g. the above urease containing products.

The object of the present invention is to provide a novel solid oral anticariogenic composition in the form of a chewing gum or a lozenge which overcomes the above disadvantages of the prior art.

The foregoing and other objects, advantages, and features of the invention are achieved by a solid oral anti cariogenic composition in the form of a chewing gum or a lozenge to be used for neutralizing acid in dental plaque subsequent to eating and drinking, which composition is characterised in that beyond the conventional chewing gum or lozenge ingredients the composition comprises as active ingredient urea or pharmacologically acceptable substances capable of releasing urea under the conditions prevailing in the oral cavity in an amount from 0.05% by weight to 80% by weight, calculated as urea, based on the total weight of the composition, an optional coating not being taken into account.

The composition according to the invention is thus remarkable for not containing hydrogen peroxide and consequently it does not conflict with the previously mentioned EEG Directive 76/768. Furthermore the composition is biologically acceptable and non-toxic (cf. the indication in the American GRAS list) the active ingredient being a natural component of the saliva. The latter also implies that the active component has an acceptable taste at oral intake in the indicated doses. The composition according to the invention increases the period of contact between urea and the teeth resulting in an improved anticariogenic effect.

Through intake of the composition subsequent to eating or drinking the caries risk is essentially reduced which has been proved through in vivo tests unambigously proving an increased pH upon chewing the composition for a certain period after the eating or drinking. The circumstance that the composition is a product to be chewed ensures firstly that the active component of the product is distributed in the mouth and reaches the sites where the anticariogenic effect is needed and where it is often difficult to clean the teeth efficiently by tooth brushing, and secondly that the stay of the product in the mouth suffizes for providing the necessary increase of the pH. Thirdly the form of the composition as a chewable product causes a saliva secretion-improving effect, and a high saliva secretion is of decisive importance to the anticariogenic effect.

The effect of the composition according to the invention has been tested using telemetric plaque pH measurements. The connection between caries and plaque pH is well-known, i.a. as described by T. Imfeld in "Identification of low caries risk dietary components, Monographs in Oral Science", vol. 11, p. 83–85, Myers, H. M. Editor, Karger, Basel, 1983, in which he reports that foodstuffs which in the plaque pH measurement system show no or only low acid production have no caries-increasing effect tested on rats and humans. On the other hand it has been shown that any foodstuff which causes caries in tests on animals and humans is also acid producing in interdental telemetric plaque pH-tests. Thus, it is generally accepted that telemetric plaque pH measurements are a significant indication of the possibility of caries development, and that a plaque acid neutralizing means is an effective anticariogenic means.

The composition according to the invention must be formulated as a chewing gum or a lozenge in order to ensure a sufficiently long stay thereof in the mouth, preferably for at least 10 minutes. In this manner the possibility of an efficient neutralization of the plaque acid produced by eating or drinking is ensured.

When a composition according to the invention is chewed or sucked immediately after eating or drinking, the desired acid-neutralizing effect in the oral cavity is obtained, and especially on sites with heavy plaque.

By using a composition according to the invention the normally occurring pH drop to a value below 5.5 usually remaining for about 30–40 minutes is eliminated. By using the composition according to the invention after each eating and drinking, and also after an additional intake within the above already critical 30–40 minutes, the further extension of the demineralisation phase is avoided.

It is a fact that the longer the demineralisation phase lasts the greater is the probability of caries.

By using the composition according to the invention in the manner described a momentaneous neutralization of the acid is ensured after eating or drinking, and the plaque pH can be kept above 5.5. The possibility of intake of a composition according to the invention implies furthermore as an additional, favourable side effect that the craving for another intake of carbohydrate such as snacks, sweets and ice no longer applies or at least is postponed.

It is assumed that the effect of the composition according to the invention is based on a co-operation of several processes. By chewing or sucking the composition the secretion of saliva and consequently the flow of saliva is multiplied in such a manner that both a dilution and a rinsing of the plaque environment take place. Furthermore the natural buffer system of the saliva implies that a certain neutralization of present acid occurs. An efficient neutralization of acid in order to maintain a pH above 5.5 is obtained by the urea content of the composition as the composition according to the invention is formulated in such a manner that its urea content is released as quickly as possible. The released urea is momentaneously converted by urease into ammonium carbonate and further into ammonia and carbon dioxide. The ammonia reacts instantaneously with any present acid and the gradually produced acid whereby the plaque pH is increased from a demineralisation-causing level below 5.5 to the remineralisation level above 5.5 where the pH is kept through continued chewing and/or sucking of the composition of the invention used.

In practice the release of urea into the saliva which functions as a vehicle can commence immediately after termination of a meal as the person in question can take one or more pieces of chewing gum or one or more lozenges without involving practical problems no matter where the person is. Contrary to the latter it is seldomly possible for a person to have his teeth brushed or his mouth rinsed with a suitable product. The immediate release of urea by using a composition according to the invention implies that it is possible to avoid the high concentration of acid usually being the major cause of caries.

The physical embodiment of the composition as a chewing gum or a lozenge implies that the carrier of the composition always alters its position in the mouth via the saliva, and thereby ensures an efficient distribution of the acidneutralizing urea even to less accessible places such as between the teeth, where debris according to experience cause a particularly high production of acid and consequently require a particularly high acid-neutralizing effect.

As previously explained it is not only important to obtain a momentaneous neutralization of acid but also to ensure that the pH does not drop below 5.5. At intake of most food and beverages a deposit of a certain portion of carbohydrate in plaque occurs. If the plaque or the carbohydrate is not removed not only an instantaneous neutralization of acid is needed but also a possibility of neutralizing the acid currently produced on account of remaining carbohydrate residues involving a risk of a drop of the pH to below 5.5.

The composition according to the invention is formulated so that the urea content thereof in combination with the puffer released by the saliva compensates to a high degree for the amount of acid present in plaque after intake of carbohydrate.

DESCRIPTION OF THE PREFERRED EMBODIMENTS

A preferred composition according to the invention contains in each dosage unit at least 5 mg of urea. In practice the intake of urea should always amount to at least 5 mg in order to ensure a sufficient effect. The necessary 5 mg can, of course, always be taken in the form of several pieces of chewing gum at a time or several lozenges or both chewing gum and lozenge. The composition according to the invention contains preferably from 0.2% by weight to 25% by weight of urea based on the weight of the total composition. In practice a content within this range gave the best results. A urea content exceeding 80% by weight is inapplicable in practice. In order to utilize the favourable effects of the composition according to the invention efficiently it is necessary to chew or suck the composition according to the invention immediately after the eating and drinking for a period sufficient for releasing the active urea ingredient in an amount suffizing for the neutralization of plaque acid. By a sufficient period is usually meant a period of at least 30 sec., preferably 10 min. There are no limits as to how long the composition can be used, but in practice it is, of course, limited how long the active chewing or sucking process is desired to continue.

The keeping of the composition in the mouth for a long time ensures in combination with the above stimulation of the secretion of saliva the advantage that the tendency to desire new snacks, sweets, cakes, ice etc. is reduced whereby the period in which the plaque pH is kept on the remineralisation level is made as long as possible.

It must be expected that most people will feel attracted to the comfortable possibility of improving the oral hygiene at the same time as they obtain a caries-reducing effect merely by taking a piece of chewing gum or a lozenge for instance after each meal. In this connection it should be mentioned that the composition according to the invention can be made extra attractive by containing various additives such as e.g. flavour additives or sweeteners. All the usual additives for chewing gums and lozenges, of course, can be used.

A chewing gum according to the invention may advantageously have the following composition:

| | |
|---|---|
| Gum base | 15–50% by weight |
| Sweetener | 40–80% by weight |
| Flavour | 0.5–4% by weight |
| Urea | 0.8–4% by weight |
| Water, Colour, etc. | 0–5% by weight | an optional coating not being taken into account.

A lozenge according to the invention may advantageously have the following composition:

| | |
|---|---|
| Sweetener | 80–99% by weight |
| Flavour | 0–4% by weight |
| Lubricant | 0–4% by weight |
| Urea | 0.6–4% by weight |
| Water, Colour, etc. | 0–4% by weight. |

When the composition according to the invention is formulated as a chewing gum, the form thereof may be chosen among any of the known types of chewing gum such as chewing gum pieces optionally coated, as well as chewing gum sticks or chewing gum of an arbitrarily desired different shape depending on the intended use. The chewing gum may be of any quality, including bubble gum. No limits exist as to the chewing gum bases applicable in the chewing gum according to the invention. Usual types of chewing gum bases such as for instance those available from L. A. Dreyfus Company or Cafosa Gum A/S are generally suitable, but specially manufactured formulations can also be used. The formulation depends on the desired type of chewing gum as described above or on the desired type of structure. Suitable raw materials for gum bases include the substances according to U.S. Chewing Gum Base Regulations—Code of Federal Regulations, Title 21, section 172.615. Such substances can be natural gum base raw materials selected from the group consisting of the families Sapotaceae, Apocynaceae, Moraceae, Euphorbiaceae, and natural rubber, or synthetic gum base raw materials selected from the group consisting of butadiene-styrene rubber, isobutylene-isoprene copolymer, paraffin, petroleum wax, polyethylene, polyisobutylene and polyvinyl acetate. Other gum base raw materials which may be incorporated in the formulation include plasticizing materials, terpene resins, antioxidants, sodium sulfate, sodium sulfide, and other substances generally recognized as safe in food.

The weight of the gum base lies in the range of from about 15 to about 90%, preferably from 30 to 40% by weight based on the weight of the total composition an optional coating not being taken into account.

The amount of further auxiliaries in chewing gum is usually from about 10 to about 85% by weight.

As examples of suitable flavours the following can be mentioned: Peppermint, wintergreen, eucalyptus, spearmint, fruit flavours and any other flavour applicable in confectionery and toothpaste, including mixtures of flavours.

As sweetening ingredient in the composition according to the invention the use of sweeteners not detrimental to the teeth is recommended. Examples thereof are sorbitol, xylitol, Lycasin® glycerol, aspartame, saccharine, cyclamate as well as mixtures thereof or mixtures thereof with other suitable sweeteners.

The composition according to the invention comprises preferably powdered sorbitol and/or xylitol in an amount from about 40 to about 80% by weight, preferably from 50 to 70% by weight.

A 70% by weight aqueous solution of sorbitol, Lycasine® and/or glycerol can advantageously be present in an amount from 0 to 30% by weight, preferably from about 0 to 15% by weight.

The active component urea has the formula $$NH_2-CO-NH_2,$$

and is a white crystalline solid with a melting point from 132° to 133° C. It is easily soluble in water, slightly soluble in ethanol and methanol, and substantially insoluble in ether and chloroform. The quality of the urea used should comply with the valid pharmacopees e.g. Pharm. Nord. 1963—USP XXI or BP 80.

Beyond urea the composition according to the invention comprises also pharmacologically acceptable substances capable of releasing urea under the conditions prevailing in the mouth. Examples thereof are: Salts and addition compounds between urea and inorganic compounds such as magnesium sulphate, calcium phosphate, sodium chloride, etc.

The urea content of the composition according to the invention varies between 0.05% by weight and 80% by weight, preferably between 0.2% by weight and 25% by weight. If the composition contains a very small amount of urea it is necessary to take a greater amount of the composition as care should always be taken that the intaken amount of urea is sufficient for neutralizing the amount of plaque acid being present. This amount is usually at least 5 mg of urea.

The weight of a dosage unit of the composition according to the invention lies usually in the range of from about 0.5 g to about 20.0 g. The following Table indicates preferred ranges of various types of the product:

| | |
|---|---|
| Chewing gums without a coating | 750–3500 mg |
| Chewing gum tablets with a sugar coating | 1200–6000 mg |
| Chewing gum sticks | 1.5–5.0 g |
| Bubble gum | 1.0–7.5 g |
| Pressed lozenges | 0.5–3.0 g |
| Cast lozenges | 0.5–3.0 g |

Apart from the fact that the lozenges according to the invention must contain lubricant and, of course, not chewing gum base, the suitable ingredients of lozenges correspond substantially to those described in connection with chewing gum.

The lozenges may, of course, contain any such additives usual for lozenges.

The invention will be further illustrated by means of the following examples of compositions of anticariogenic compositions for oral administration in the form of chewing gums or lozenges.

EXAMPLES

Example 1

A non-coated chewing gum of the following composition:

| Ingredients | % by weight |
|---|---|
| Chewing gum base | 42.0 |
| Xylitol powder | 54.5 |
| Wintergreen flavour | 2.25 |
| Urea | 1.25 |

Of 80 g of the above composition 100 pieces of chewing gum were produced, each piece containing 10 mg of urea.

Example 2

A non-coated chewing gum of the following composition:

| Ingredients | % by weight |
|---|---|
| Chewing gum base | 35.5 |
| Sorbitol powder | 51.5 |
| Lycasine ® | 10.0 |
| Spearmint flavour | 2.0 |
| Urea | 1.5 |

Of 100 g of the above composition 100 pieces of chewing gum were produced, each piece containing 15 mg of urea.

Example 3

A non-coated chewing gum of the following composition:

| Ingredients | % by weight |
|---|---|
| Chewing gum base | 37.5 |
| Sorbitol powder | 53.0 |
| Glycerol | 5.0 |
| Peppermint flavour | 2.0 |
| Urea | 2.5 |

Of 80 g of the above composition 100 pieces of chewing gum were produced, each piece containing 20 mg of urea.

Example 4

| Ingredients | % by weight |
|---|---|
| Chewing gum base | 40.0 |
| Xylitol | 52.5 |
| Glycerol | 3.0 |
| Eucalyptus flavour | 2.5 |
| Urea | 2.0 |

Of 100 g of the above composition 100 pieces of chewing gum were produced, each piece containing 20 mg of urea.

Example 5

| Ingredients | % by weight |
|---|---|
| Chewing gum base | 35.5 |
| Sorbitol powder | 44.5 |
| Sorbitol 70% | 15.0 |
| Spearmint | 2.0 |
| Urea | 3.0 |

Of 100 g of the above composition 100 pieces of chewing gum were produced, each piece containing 30 mg of urea.

Example 6

| Ingredients | % by weight |
|---|---|
| Chewing gum base | 31.0 |
| Sorbitol powder | 52.0 |
| Lycasine ® | 15.0 |
| Fruit flavour | 1.0 |
| Urea | 1.0 |

Of 300 g of the above composition 100 pieces of chewing gum were produced, each piece containing 30 mg of urea.

Example 7

In order to ensure the proper taste, appearance, protection of the content as well as the packaging system the chewing gum tablets prepared according to the Examples 1–6 are coated with a real coating (dragée layer) and/or a thin surface layer by polishing or application of a film according to A, B or C:

A: Sorbitol as a 70% solution

B: Xylitol 70.0%
Water 30.0%

C: Carnauba wax 25 g
Bees' wax 25 g optionally admixed colour, pigment, binder and/or additional water.

The surface layer was applied by means of a conventional dragée vessel until the desired weight per piece was obtained.

Example 8

Bubble gum of the following composition was prepared:

| Ingredients | % by weight |
| --- | --- |
| Chewing gum base | 20.0 |
| Sorbitol powder | 68.2 |
| Sorbitol 70% | 10.0 |
| Flavour | 0.8 |
| Urea | 1.0 |

Of 500 g of the above composition 100 pieces of bubble gum were produced, each piece containing 50 mg of urea.

Example 9

Chewing gum sticks of the following composition were prepared:

| Ingredients | % by weight |
| --- | --- |
| Chewing gum base | 25.0 |
| Sorbitol powder | 64.0 |
| Lycasine ® | 10.0 |
| Flavour | 1.0 |
| Urea | 1.0 |

Of 300 g of the above composition 100 chewing gum sticks were prepared, each stick containing 30 mg of urea.

Example 10

Lozenges of the following composition were prepared by compressing:

| Ingredients | % by weight |
| --- | --- |
| Sorbitol powder | 96.5 |
| Peppermint flavour | 0.5 |
| Magnesium stearate | 1.0 |
| Urea | 2.0 |

The ingredients were mixed and tabletted by means of a conventional tabletting machine.

Of 100 g of the composition 100 tablets were prepared, each tablet containing 20 mg of urea.

Example 11

Lozenges of the following composition were cast:

| Ingredients | % by weight |
| --- | --- |
| Gum arabicum | 35.0 |
| Sorbitol | 62.7 |
| Peppermint flavour | 0.3 |
| Urea | 2.0 |

The ingredients were mixed and cast into lozenges of about 1.5 g, each lozenge containing 20 mg of urea.

Example 12

Chewing gum pieces of the following composition were prepared:

| Ingredients | % by weight |
| --- | --- |
| Chewing gum base | 37.5 |
| Sorbitol powder | 51.5 |
| Glycerol | 5.0 |
| Peppermint flavour | 2.0 |
| Urea calcium sulphate addition compound $4(CH_4N_2O).CaSO_4$ | 4.0 |

Of 80 g of the above composition 100 pieces of chewing gum were prepared, each piece containing 28 mg of $4(CH_4N_2O).CaSO_4$ and being capable of releasing 20 mg of urea.

In the Examples 1–11 one or more alternative pharmacologically acceptable substances capable of releasing urea under the conditions prevailing in the oral cavity including e.g. the above mentioned addition compound may substitute the urea. In case of such substitution, the amount of urea used in the composition in question should, of course, be substituted an amount of the urea releasing substance which is able to release the equivalent amount of urea.

Further examples of substances that may be used are $$6(CH_4N_2O).MgSO_1.2H_2O \text{ and } CH_4N_2O.NaCl.H_2O.$$

Examples of equivalent amounts are:

| | |
| --- | --- |
| $6(CH_4N_2O).MgSO_4.2H_2O$ | 1.4 times the indicated amount of urea |
| $4(CH_4N_2O).CaSO_4$ | 1.6 times the indicated amount of urea |
| $CH_4N_2O.NaCl.H_2O$ | 2.3 times the indicated amount of urea. |

Test Results

The anticariogenic effect of the composition according to the invention has been verified by the following tests.

Initially tests were carried out with the purpose of determining the optimum urea content in a dosage unit of the composition according to the invention.

Dosage units with a urea content of 0, 5, 10, 15, 20, and 30 mg of urea, respectively, were tested by intake immediately after a previous intake of sugar in the form of a sucrose rinse.

Telemetric plaque pH measurements were performed on test persons during the period after the sugar rinse as mentioned above, followed by a 10 min. chewing of the tested product according to the invention. The plaque pH measuring continued for 30 min. after this chewing period. The results disclosed that the best effect was obtained by a dosage unit containing 20 mg of urea. Already by 5 mg of urea a clear pH-increasing effect was detected, said effect being significantly better than the effect obtained by compositions free of urea. A urea content beyond 20 mg per dosage unit rendered no further essential advantages.

Comparative Tests

Clinical tests have been carried out at the Dental Institute, University of Zürich, Department of Cardiology, Periodontology and Preventive Dentistry Bioelectronic Unit, under the leadership of Dr. T. Imfeld. By these tests the following three testing sequences were compared:

1) Rinsing for two minutes with a sucrose solution (15 ml, 0.3 mol/l), followed by a monitored period of 30 minutes.

2) Rinsing with a sucrose solution as used in 1) for two minutes, 15 minutes rest period 10 minutes chewing of a conventional sucrose-free sorbitol-sweetened chewing gum (Gum 31) and then a monitored period of 30 minutes.

3) The same testing sequence as for 2) but with a sucrose-free, sorbitol-sweetened chewing gum containing 20 mg urea (Gum 32).

Prior to each testing sequence the test persons chewed a neutral paraffin for about 3 minutes followed by a resting period of about 15 minutes.

Five persons were tested using the latin square system, each testing sequence being repeated three times for each person.

The tests were performed as double blind tests.

The telemetric measurement, the plaque pH, was monitored and recorded during the entire testing sequences.

Table I below shows the immediate neutralizing activity during chewing of the two gums expressed by the difference in plaque pH between the lowest value reached after the sucrose rinse and the highest value reached during subsequent gum chewing, and the prolonged neutralizing effect of the gums expressed by the difference in plaque pH between the lowest value reached after the sucrose rinse and the lowest value reached during the 30 minutes' monitored period after gum chewing. The result shown in Table I is the average obtained from the 15 testing sequences.

TABLE I

|  | Immediate neutralizing activity (Δ pH) | Prolonged neutralizing effect (Δ pH) |
| --- | --- | --- |
| Gum 31 Comparison gum | 1.81 | 0.95 |
| Gum 32 according to the invention | 2.35 | 1.14 |

The prolonged neutralizing effect can also be expressed on the basis of the square surfaces (pH×minute) obtained from curves where the plaque pH is plotted against the time. The square surfaces limited by the pH-curves above pH 5.7 and a horizontal line at pH 5.7 during the 30 minutes monitored period after chewing of the gums and after a sucrose rinse (testing sequence 1), control) demonstrate the accumulated period above the critical pH 5.7, i.e. on the safe side of the critical level.

On the basis of the same pH-curves the square surfaces (pH×minute) limited by the pH-curves below pH 5.7 and a horizontal line at pH 5.7 during the 30 minutes monitored period after chewing of the gums and after a sucrose rinse (control) gives a combined accumulation of the time and distance below the critical pH 5.7 level, i.e. a combined measure of the caries rist. The average values from 15 testing sequences are shown in Table II:

TABLE II

|  | Surface area (pH × min) above pH 5.7 | Surface area (ph × min) below pH 5.7 |
| --- | --- | --- |
| Gum 31 comparison Gum | 6.85 | 11.82 |
| Gum 32 according to the invention | 14.46 | 6.64 |
| Control | 0.13 | 64.73 |

The following conclusion can be made on the basis of the results shown in Table I and Table II:

1) If a test person takes easily fermentable carbohydrates such as sucrose the dental enamel will be exposed to demineralisation for 30–40 minutes.

2) If a test person with plaque chews sucrose-free chewing gum after intake of easily fermentable carbohydrates an almost instantaneous neutralization occurs (gum 31). During a chewing period of 10 minutes the pH rises to values above the critical pH 5.7, where a remineralisation occurs. However, it drops below the critical value by the end of the chewing period.

3) If 20 mg urea have been added to the sucrose-free chewing gum, both an increased instantaneous neutralization and an increased prolongation of the neutralization occur. It appears that pH does not drop below the critical value (5.7) during the chewing period (gum 32).

It can be concluded that a sucrose-free chewing gum having 20 mg urea is far more efficient for neutralizing acidified plaque layers in humans compared to a sucrose-free chewing gum without urea.

I claim:

1. A solid, oral, anticariogenic, chewable piece of chewing gum comprising:

a chewing gum base made from at least one substance selected from the group consisting of natural or synthetic gum bases of the families Sapotaceae, Apocynaceae, Moraceae, Euphorbiaceae, natural rubber, butadiene-styrene rubber, isobutylene-isoprene copolymer, paraffin, petroleum wax, polyethylene, polyisobutylene and polyvinyl acetate;

taste enhancers selected from the group consisting of peppermint, wintergreen, eucalyptus, spearmint, fruit flavors, sorbitol, xylitol, Lycasin®, glycerol, aspartame, saccharine, and cyclamate as well as mixtures thereof; and urea for neutralizing acid in dental plaque subsequent to eating or drinking, said urea being present in an amount in the range of 5–30 mg per said piece of chewing gum.

2. A chewing gum in accordance with claim 1 containing color components.

* * * * *

UNITED STATES PATENT AND TRADEMARK OFFICE
CERTIFICATE OF CORRECTION

PATENT NO. : 5,470,566

DATED : November 28, 1995

INVENTOR(S) : Claude E. Lützen

Page 1 of 2

It is certified that error appears in the above-indentified patent and that said Letters Patent is hereby corrected as shown below:

```
Col. 1, line 30, change "isdivided" to --is divided--
Col. 2, line 13, change "1970/ 1971" to --1970/1971--
        line 41, change "the-bag" to --the bag--
Col. 3, line 11, change "oral" to --Oral--
        line 17, change "odont." to --Odont.--
        line 27, change "to8.5" to --to 8.5--
        line 58, change "flatter" to --latter--
Col. 4, line 14, change "50°60°" to --50-60°--
        line 18, change "80°" to --80° C--
        line 56, change "Directire" to --Directive--
        line 62, after "chewing" insert --gums--
```

UNITED STATES PATENT AND TRADEMARK OFFICE
CERTIFICATE OF CORRECTION

PATENT NO. : 5,470,566
DATED : November 28, 1995
INVENTOR(S) : Claude E. Lutzen

It is certified that error appears in the above-indentified patent and that said Letters Patent is hereby corrected as shown below:

Col. 5, line 18, change "EEG" to —EEC—
Col. 8, line 20, change "Regulations-Code" to —Regulations Code—
      line 53, change "Lycasine®" to —Lycasin®—
Col. 9, line 65, change "Lycasine®" to —Lycasin®—
Col. 10, line 62, change "Lycasine®" to —Lycasin®—
Col. 11, line 44, change "Lycasine®" to —Lycasin®—
Col. 14, line 11, change "rist" to —risk—

Signed and Sealed this

Seventh Day of January, 1997

Attest:

*Attesting Officer*

BRUCE LEHMAN
Commissioner of Patents and Trademarks